United States Patent [19]
Kroll et al.

[11] Patent Number: 5,607,460
[45] Date of Patent: Mar. 4, 1997

[54] PHYSICIAN INTERFACE EXPERT SYSTEM FOR PROGRAMMING IMPLANTABLE ARRYTHMIA TREATMENT DEVICES

[75] Inventors: Mark W. Kroll, Minnetonka; James E. Brewer, Maplewood; Scott T. Armitage, Minnetonka, all of Minn.

[73] Assignee: Angeion Corporation, Plymouth, Minn.

[21] Appl. No.: 616,256

[22] Filed: Mar. 15, 1996

[51] Int. Cl.$^6$ .................................................. A61N 1/362
[52] U.S. Cl. ................................................ 607/30; 607/59
[58] Field of Search ................................. 607/30, 59, 14; 128/705, 697

[56] References Cited

U.S. PATENT DOCUMENTS

| | | | |
|---|---|---|---|
| 4,726,380 | 2/1988 | Vollmann | 607/30 |
| 4,825,869 | 5/1989 | Sasmor et al. | 607/27 |
| 5,226,413 | 7/1993 | Bennett et al. | 607/30 |
| 5,292,341 | 3/1994 | Snell | 607/30 |
| 5,421,830 | 6/1995 | Epstein et al. | 607/30 |

Primary Examiner—William E. Kamm
Assistant Examiner—George R. Evanisko
Attorney, Agent, or Firm—Brad D. Pedersen

[57] ABSTRACT

The present invention is a physician's interface expert system that allows a physician not well versed in ICD parameters to program at least one parameter into an ICD using the physician's existing knowledge of the patient's medical history. The programmable ICD system is composed of an implantable portion and a programming device external from the patient's body. The implantable portion has pulse generating circuitry, control circuitry including parameter storage, a receiver and at least one electrical lead for placement in the patient's heart. The programming device contains an operator interface device that receives a first set of values from the operator. A translator is provided in the programming device for translating the first set of values into a second set of values formatted in accordance with the programmable parameter settings of the implanted device. Finally, a transmitter is provided in the programming device to transmit the second set of values to the receiver of the implanted device.

11 Claims, 4 Drawing Sheets

PHYSICIAN INTERFACE EXPERT SYSTEM FOR PROGRAMMING IMPLANTABLE ARRYTHMIA TREATMENT DEVICES

FIELD OF THE INVENTION

The present invention is related to programmable implantable cardioverter defibrillators (ICDs). In particular, the present invention is an expert system for programming ICDs such that a first set of values may be entered by a physician into a programmer and a second set of values are then transmitted from the programmer to the ICD.

BACKGROUND OF THE INVENTION

The use of implantable cardioverter defibrillator (ICD) systems as a medical therapy for persons with abnormal heart conditions or cardiac arrhythmias is well known. Initially, ICD systems were used only to resuscitate or defibrillate a heart which had stopped pumping because there was no organized heart beat. This type of arrhythmia, referred to as ventricular fibrillation (VF), is relatively simple to detect and is fatal if not corrected in a few minutes. The general approach in using ICD systems to treat ventricular fibrillation is to deliver a relatively large electrical defibrillation countershock to electrodes implanted about the heart in an attempt to restart the electrical activity of the heart. In existing ICD systems, the defibrillation electrical countershocks are in the range of 25 to 40 joules, and are generated by high voltage capacitors within the ICD system that are charged to approximately 600 to 750 volts by one or more internal batteries.

ICD systems are now being used to treat other types of abnormal heart conditions, such as the main pumping chambers of the heart beating too fast. This type of arrhythmia, referred to as ventricular tachycardia (VT) can be clinically divided into two subclasses. The first VT subclass is a low rate ventricular tachycardia where the heart is beating in the range of approximately 120 to about 180 beats per minute. While a low rate VT is not normal, the patient is not in immediate danger of dying because there is still a perfusing pulse that can pump blood to the body. The second VT subclass is a high rate ventricular tachycardia where the heart is beating in the range of approximately 180 to about 250 beats per minute. In contrast to low rate VT, a patient with a high rate VT is in imminent danger of death within the next several minutes due to a significantly diminished or absent perfusing pulse.

High rate VT, despite its severity and grim prognosis, is treated differently from ventricular fibrillation. This is because, unlike a VF arrhythmia where there is no organized electrical activity of the heart, a high rate VT arrhythmia still exhibits a fairly organized and synchronous electrical activity of the heart and often can be treated by delivering a synchronized "cardioversion" countershock of lower energy that is in the range of 1 to 5 joules. If this cardioversion countershock is unsuccessful, existing ICD systems immediately resort to the use of a defibrillation countershock due to the serious nature of the high rate VT arrhythmia.

Low rate VT is also characterized by a synchronized electrical activity of the heart, but a low rate VT is usually able to generate a perfusing pulse. As a result, it is important in treating a low rate VT to avoid subjecting the patient to an electrical cardioversion therapy that could convert the patient from an abnormal, but life sustaining arrhythmia, to an abnormal and terminal arrhythmia. Because a low rate VT is not immediately life-threatening, avoidance of shock pain is a major goal. Thus, the usual approach for low rate VT is to deliver bursts of overdrive pacing pulses that will pace the heart at a rate greater than the low rate tachycardia. This technique utilizes pacemaker level energies of approximately 10 to 50 microjoules per pulse for a burst duration of approximately 10 pulses per burst. If the first burst is unsuccessful and the patient remains in a low rate VT, subsequent bursts are reattempted.

An ICD system is more than just a pulse-generating device that is implanted in the patient. The pulse-generating ICD is a part of a collection of electrical and mechanical components of an entire ICD system. The parts of the system include; the ICD itself, leads, a test instrument, and a programmer among other things. The programmer is the physician's window to the operation and the programmable settings of the ICD. The programmer allows a physician, usually a highly trained ICD specialist, or electrophysiologist (EP), to enter numerous parameters related to the operation of the ICD for each individual patient.

Because of the unique requirements of each patient and the different kinds of therapies to be delivered, there are numerous parameters that need to be programmed into the ICD, such as fibrillation detection rate, high rate tachycardia detection rate, and rate cutoff for low rate ventricular tachycardia, just to name a few. Clinical physicians understand a patient's medical history, but are not necessarily familiar with all of the ramifications and combinations of all of the parameters that need to be programmed into an ICD. Additionally, the parameters, in many cases, are not given in rates that the physician is familiar with, such as beats per minute, but rather are given as intervals such as 333 ms. Therefore, the physician must translate familiar units into unfamiliar alternate units when programming an ICD, a process which can be time consuming and difficult.

More importantly, except for the highly experienced ICD implanter, the physician may not be aware of the critical importance of setting a detection rate accurately as opposed to setting it 10% higher or lower than it should be. Accurate settings in an ICD are critical in applying an appropriate therapy. Setting a defibrillation or cardioversion detection rate too low may cause an unrequired defibrillation or cardioversion countershock to the heart which is both very painful and potentially damaging to the heart. Setting a detection rate too high may cause the failure to timely apply a countershock to a fibrillating heart and thus may allow a patient to die.

It would be desirable to provide an ICD system capable of being automatically programmed by a physician familiar with a patient's medical history, yet who may not know each and every parameter setting for ICD programming.

SUMMARY OF THE INVENTION

The present invention is a physician's interface expert system that allows a physician not well versed in choosing among various ICD parameters to program at least one parameter into an ICD using the physician's existing knowledge of the patient's medical history. The programmable ICD system is composed of an implantable portion and a programming device external from the patient's body. The implantable portion has pulse generating circuitry, control circuitry including parameter storage, a receiver and at least one electrical lead for placement in the patient's heart. The programming device contains an operator interface device that receives a first set of values from the operator. A translator is provided in the programming device for translating the first set of values into a second set of values formatted in accordance with the parameter settings of the implanted device. Finally, a transmitter is provided in the programming device to transmit the second set of values to the receiver of the implanted device.

DETAILED DESCRIPTION OF THE DRAWINGS

The present invention is a physician interface expert system. The expert system is designed to allow a physician who is familiar with a patient's medical history to program at least one parameter into an implantable cardioverter defibrillator (ICD) without having to know each and every parameter necessary for programming the ICD and without having to convert into the units of the parameters stored within the ICD.

Figure 1:
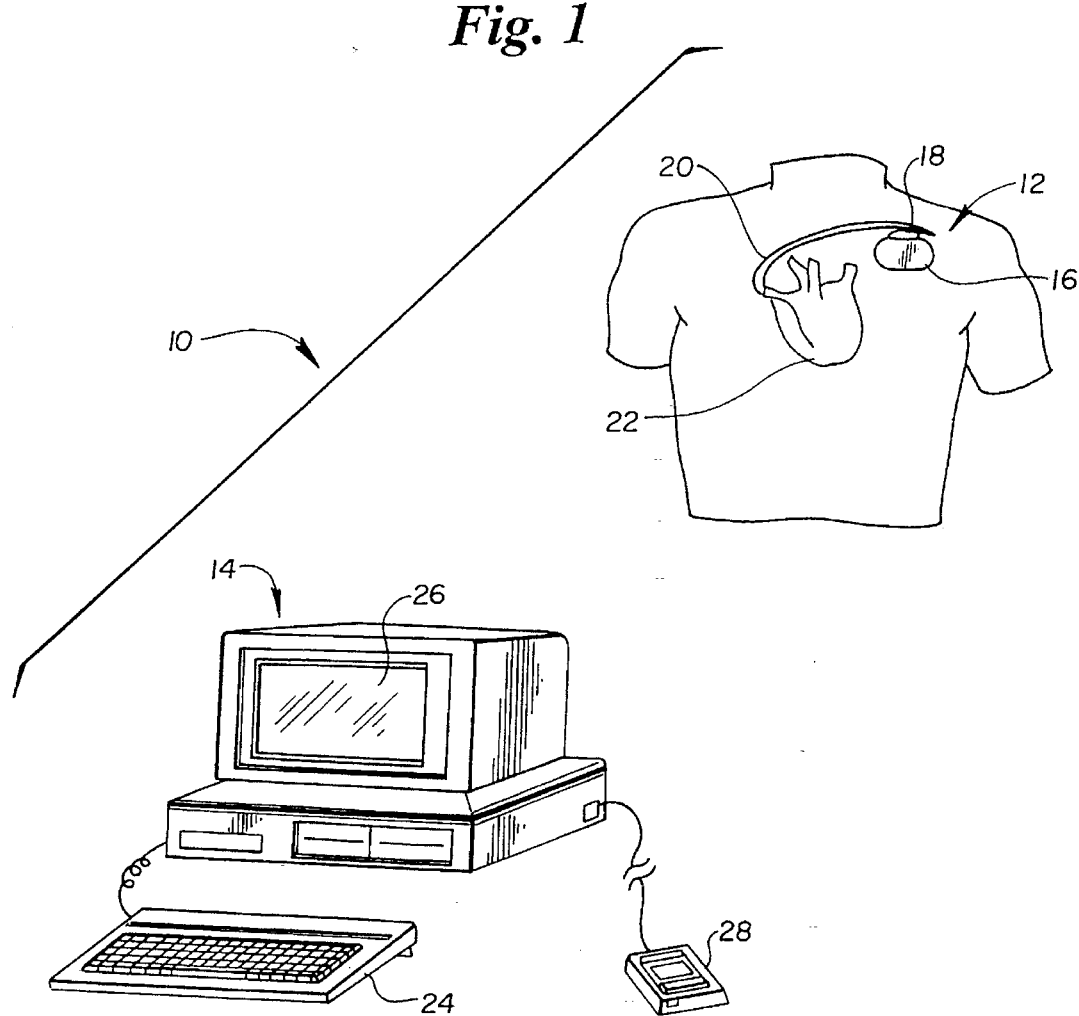
FIG. 1 is a schematic illustration of an implantable cardiac defibrillator system having a housing portion implanted in a patient and an operator interface device external the patient.

A programmable ICD system is illustrated generally at 10 in FIG. 1. The system has an implantable ICD portion 12 and a programming portion 14 external to the patient. The ICD portion 12 has a housing 16 with a header 18 mounted to the housing, and at least one electrical lead 20 connected to header 18. As illustrated in FIG. 1, electrical lead 20 may be positioned inside the patient's heart 22. ICD 12 is a standard ICD containing pulse generating circuitry, control circuitry including parameter storage and a receiver, none of which are illustrated in FIG. 1, but may be seen schematically in FIG. 2.

Programming device 14 comprises an input device 24, an operator interface device 26 and a transmitter 28. The input device in the present invention is illustrated as a keyboard, but other known interface devices may also be used without departing from the spirit or scope of the invention. Likewise, while a monitor is illustrated as operator interface device 26, other such devices for outputting information to an operator could also be used, such as a printer, without departing from the spirit or scope of the invention. Transmitter 28 is a low powered remote signal transmitter for transmitting information from programming device 14 to ICD 12.

Figure 2:
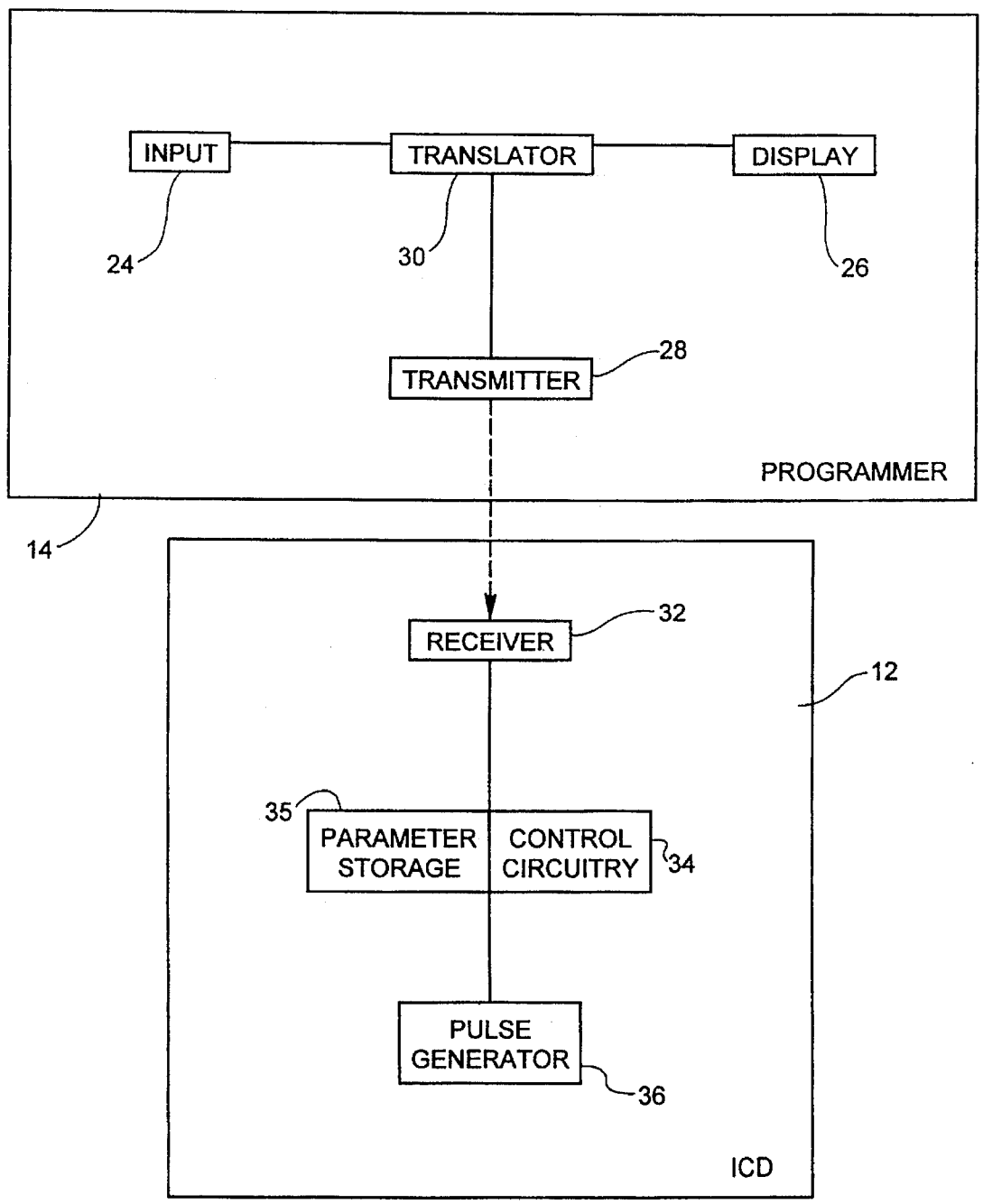
FIG. 2 is a block diagram of the housing and the programmer of FIG. 1.

FIG. 2 is a block diagram that illustrates the component parts of programmer 14 and ICD 12. As described with reference to FIG. 1, programmer 14 contains an input device 24, a display 26, and a transmitter 28. Programmer 14 also contains a translator 30. In the preferred embodiment, translator 30 is a microprocessor that converts a first set of data into a second set of data as will be described in greater detail below. As stated above, the ICD contains a receiver 32, control circuitry 34 including parameter storage 35 and a pulse generator 36.

The present invention is designed to allow a physician who is familiar with a patient's medical history to program an ICD using terms and conditions the physician is already familiar with. For instance, a physician is usually familiar with the following medical conditions of a patient experiencing heart problems: age, weight, height, sex, ventricular tachycardia history, ventricular fibrillation history, a trial fibrillation history, the existence of a coronary artery disease, cardiomyopathy, smoker/non-smoker, drinker/non-drinker, cholesterol level, lipid profile, electrolyte profile, history of drug abuse, chest pain systems, history of sudden death in the family, rate of ventricular tachycardia, prescription drug profile, ventricular tachycardia morphology and PVC count. This list is not meant to be an exhaustive list, but only a representative list of conditions a physician may be aware of.

While it is important to understand a patient's medical history, these medical conditions are not the parameters used to program an ICD. Parameters typically programmed into an ICD include: tachycardia detection rate, fibrillation detection rate, stability algorithms, fast ventricular tachycardia rate, bradycardia rate, stability algorithm settings, onset algorithms, specific therapies programmed for each zone, and the duration of the therapy needed for each zone. Once again, this is only a representative list, and is not meant to be an exhaustive or exclusive list.

The present invention allows the physician to enter the medical history of the patient into programmer 14 via input device 24. Once inside programmer 14 the medical history information is translated by translator 30 into data formatted in accordance with the programmable parameter settings of ICD 12. The parameter data is then transmitted by transmitter 28 to receiver 32 in ICD 12. The information is then stored in parameter storage 35 of control circuitry 34 for proper operation of the ICD.

Figure 3A:
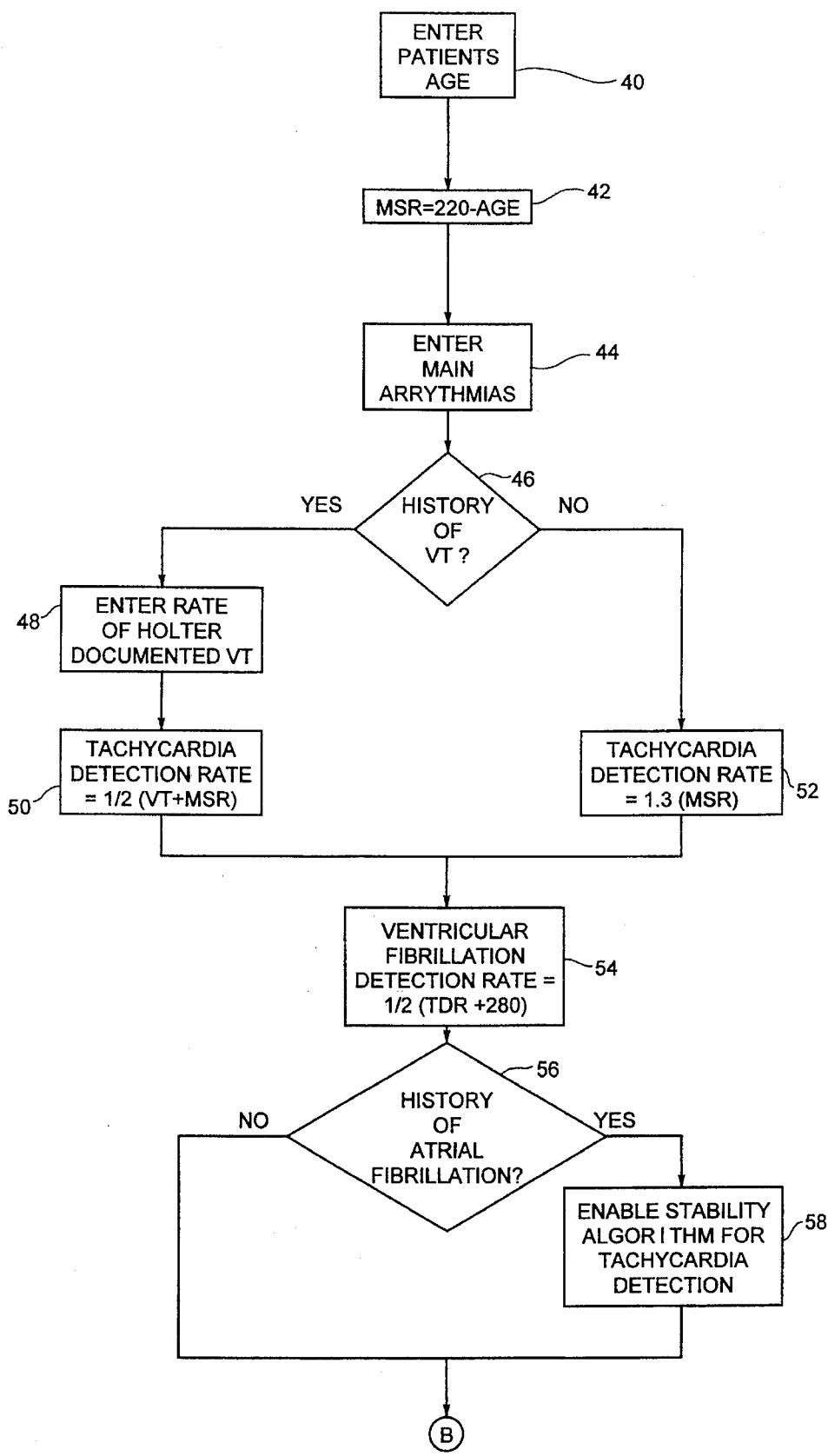
FIGS. 3A and 3B are a flow chart of a method of operation of the present invention.
Figure 3B:
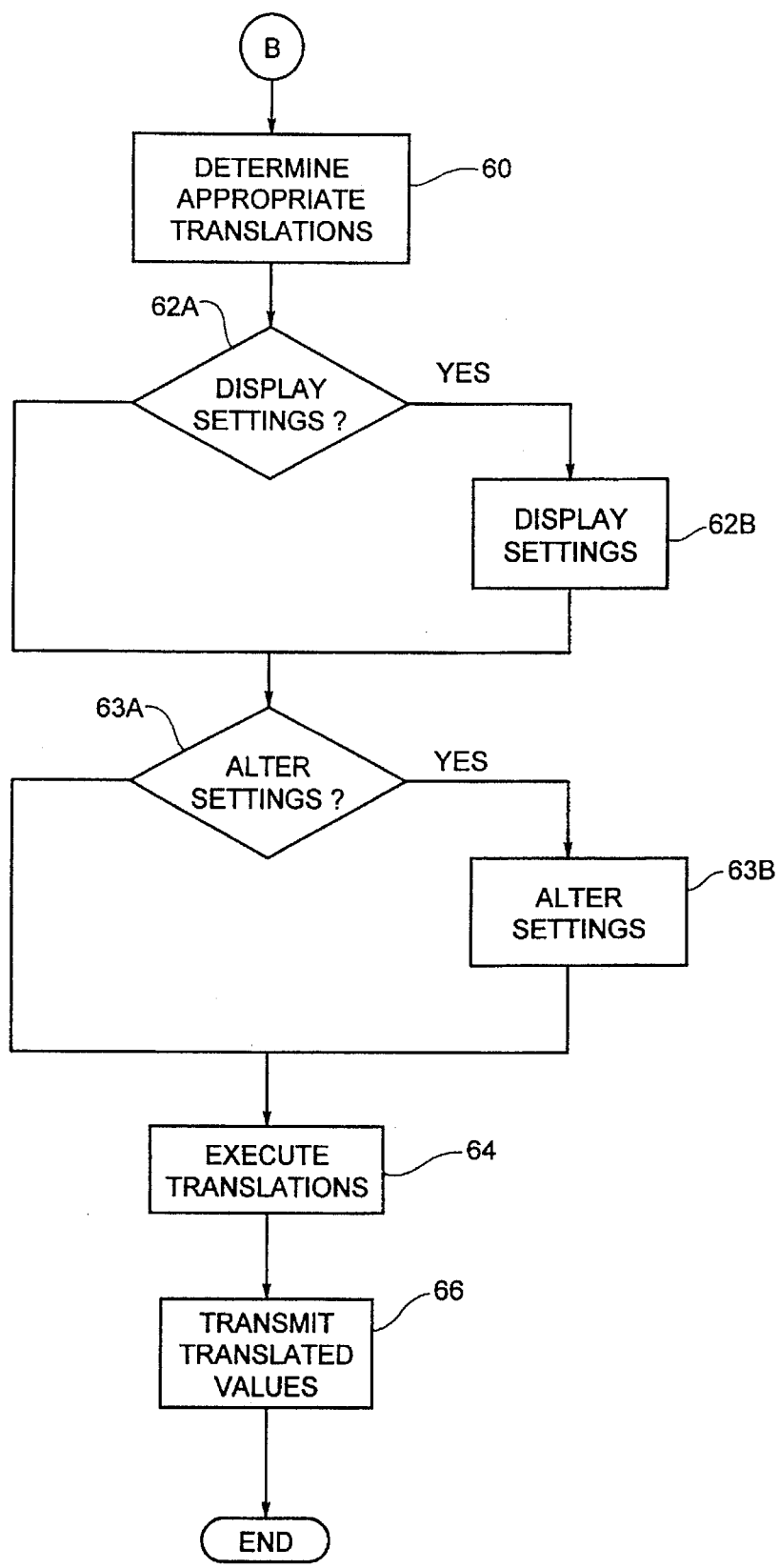

FIGS. 3A and 3B illustrate an example of a specific subroutine for setting the tachycardia detection rate and the fibrillation detection rate based on inputted medical data by a physician. The first step is that programmer 14 prompts the physician, or whoever is operating the programmer, to enter the patient's age. This step is illustrated in block 40. Once the patient's age has been entered, the programmer then calculates the maximum sinus rate (MSR) by subtracting the age from 220 beats per minute. For example, if the patient's age is 62, then the MSR will be calculated to be 158 beats per minute. 220 beats per minute has been chosen as the baseline number because it gives an accurate rule of thumb for an upper limit for the patient's heart rate under normal exercising conditions. It should be noted, however, that greater or lesser values may be chosen in place of 220 beats per minute without departing from the spirit or scope of the invention. For example, other patient historical factors could also be polled and the results of that polling can be used to alter the base value of 220 beats per minute from which the MSR is calculated. Similarly, other patient historical factors could be used to create a new effective age for a patient prior to subtracting the patient's age from the base value to obtain the MSR.

Block 44 prompts the physician to enter the main arrhythmias of the patient, typically ventricular tachycardia (VT) and/or ventricular fibrillation (VF). Decision block 46 then prompts the physician to enter yes or no to the question of whether there has been history of ventricular tachycardia in this particular patient. If yes, the subroutine branches to block 48 which prompts the physician to enter the rate of the Holter documented VT. Typically, a patient with a history of ventricular tachycardia has had this documented by wearing a Holter or ambulatory EKG machine. By examining the paper print out or semiconductor memory from such a device, it is easy to ascertain the patient's heart rate during the VT. This is the rate that is asked for in block 48. In block 50, the tachycardia detection rate is calculated as the average of the documented VT rate and the maximum sinus rate.

If, on the other hand, back at decision block 46, there was no history of ventricular tachycardia in this particular patient, the tachycardia detection rate is simply set at 30% higher than the MSR, as is illustrated in block 52. Since there has been no history of VT, there has probably been no cause for the patient to have worn a Holter or ambulatory EKG machine. Therefore, it is doubtful that the physician would know the VT rate for this patient. Studies have found that in approximately 40% of patients rescued by paramedics with external fibrillation actually go on to have tachycardia episodes, which means these patients probably had a tachycardia episode prior to going into fibrillation. By setting the detection rate at 30% higher than the MSR, appropriate tachyrhythmia therapy can be delivered in anticipation that a number of these fibrillation episodes can thereby be avoided. It will be recognized that other patient historical factors could be used to alter the value of 30% higher than the MSR for the tachycardia detection rate.

Regardless of which path is taken from decision block 46, the ventricular fibrillation detection rate is then calculated in block 54. The VF detection rate is set at the average of the tachycardia detection rate and 280 beats per minute. This insures that a ventricular fibrillation will be detected since the effective rate of VF is nearly 280 beats per minute or more, yet a lower rate tachycardia will be prevented as being Classified as fibrillation. Again, historical patient factors can be polled to alter this value.

The next step is illustrated in decision block 56 where the physician is prompted to enter whether or not there is a history of atrial fibrillation in this particular patient. If there is a history of atrial fibrillation, programmer 14 will enable a stability algorithm for tachycardia detection. A stability algorithm uses the rate stability to differentiate between atrial fibrillation and ventricular tachycardia. Specifically, atrial fibrillation produces a very irregular rate in the ventricle. Thus, the high ventricular rate due to atrial fibrillation can be classified as atrial fibrillation rather than ventricular tachycardia due to the fact that the rate is relatively unstable.

After the stability algorithm has been enabled in block 58 or if there is no history of atrial fibrillation, the subroutine determines the appropriate translation of the parameters for the ICD, as illustrated in block 60. At this point, the programmer has calculated the appropriate VF and VT detection rates for the particular patient. At blocks 62a and 62b, the rates and settings are optionally displayed to the physician for confirmation. Alternately, a physician may override the calculated settings and insert other values for the VF and VT detection rates as illustrated at blocks 63a and 63b. At block 64, the rates and the settings are translated from beats per minute to duration values, for example. This translation will be dependant upon the particular parameter format for the ICD device being programmed. At block 66, transmitter 28 sends the parameters to receiver 32. Receiver 32 then passes the parameters along to control circuitry 34 where they are stored in parameter storage 35. ICD 12 is now programmed with patient specific VF and VT detection rates.

While it may be suggested that the translation be done inside the housing of the ICD, there are a number of reasons to do it externally. One reason is that the processing power of the ICD is not designed for numerical manipulation applications such as the translation process. Another reason is that if an additional or more powerful microprocessor were added to handle the additional computations, there would be an additional power consumption. An additional power consumption usually translates into increasing the size of components and increasing heat dissipation capabilities. ICD designers are looking for ways to reduce component size, not to increase component size.

It should be noted that it would also be possible to utilize Neural Net or some other "off the shelf" expert system to assist in the translation routine. It should also be noted that other aspects of ICD programming can be performed in accordance with the teachings of the present invention. For example, the parameters for the anti-tachycardia pacing and the defibrillation shock may also be done in a similar manner.

We claim:

1. A programmer for programming an implantable cardioverter defibrillator (ICD) comprising:

an input device that receives a first set of values including historical and observed patient profile information for a particular patient into whom the ICD is to be implanted;

a translator that translates the first set of values that are not formatted in accordance with a range of programmable parameter settings of the ICD to be implanted into a second set of values that are formatted in accordance with the range of programmable parameter settings of the ICD to be implanted; and a transmitter that transmits the second set of values to the ICD to be implanted.

2. A programmable implantable cardiac arrhythmia therapy system comprising:

an implantable cardiac arrhythmia therapy device having pulse generating circuitry, a control portion including parameter storage, a receiver, and at least one electrical lead, the implantable cardiac device being implantable within a patient's body; and a programming device external from the patient's body, the programming device comprising:

an input device that receives a first set of values from an operator; the first set of values including historical and observed patient profile information for a particular patient into whom the implantable cardiac device is to be implanted;

a translator that translates the first set of values that are not formatted in accordance with a range of programmable parameter settings of the implantable cardiac device into a second set of values that are formatted in accordance with the range of programmable parameter settings of the implantable cardiac device; and a transmitter that transmits the second set of values to the receiver of the implantable cardiac device.

3. The system as in claim 2 wherein the implantable cardiac arrythmia therapy device is an implantable cardioverter defibrillator (ICD).

4. A programmable implantable cardiac arrhythmia therapy system comprising:

an implantable cardiac arrhythmia therapy device having pulse generating circuitry, a control portion including parameter storage, a receiver, and at least one electrical lead; and a programming device external from a patient's body, the programming device comprising:

an input device that receives a first set of values from an operator wherein the first set of values are selected from a group of patient profile parameters consisting of: age, sex, weight, height, ventricular tachycardia in the past, ventricular fibrillation in the past, atrial fibrillation in the past, coronary artery disease, cardiomyopathy, smoker, drinker, cholesterol level, lipid profile, electrolyte profile, prescription drug history, chest pain symptoms, history of sudden death in the family, rate of ventricular tachycardia, drug abuse, ventricular tachycardia morphology and PVC count or any combination thereof;

a translator connected to the input device that translates the first set of values into a second set of values wherein the second set of values are selected from the group consisting of: tachycardia detection rate, fibrillation detection rate, stability algorithms, fast ventricular tachycardia rate, bradycardia rate, stability algorithm settings, onset algorithms, individual therapies for each zone, and duration of therapies for each zone or any combination thereof; and a transmitter connected to the translator that transmits the second set of values to the receiver.

5. The system as in claim 4 wherein the implantable cardiac arrythmia therapy device is an implantable cardioverter defibrillator (ICD).

6. The system as in claim 4 wherein the transmitter is a wireless transmitter for remote communication with the implantable device.

7. A method of programming an implantable cardiac arrythmia device adapted for implantation in a human patient containing pulse generating circuitry, a control portion including a parameter storage device, a receiver and at least one electrode lead, using a programming device external from the patient's body having an input device, a translator connected to the input device and a transmitter connected to the translator, the method comprising the steps of:

prompting an operator for a first set of data entry values the first set of values including historical and observed patient profile information for a particular patient into whom the implantable cardiac device is to be implanted;

calculating a second set of data parameter values based upon the first set of data entry values that are not formatted in accordance with a range of programmable parameter settings of the implantable cardiac device wherein the second set of data values are formatted in accordance with the range of programmable parameter settings of the implantable device; and transmitting the second set of data values to be received by the implanted cardiac arrhythmia device.

8. The method of claim 7 further comprising the step of storing the second set of data values in the parameter storage device.

9. The method of claim 7 further comprising the step of selecting the first set of data entry values from the set of: age, sex, weight, height, ventricular tachycardia in the past, ventricular fibrillation in the past, atrial fibrillation in the past, coronary artery disease, cardiomyopathy, smoker, drinker, cholesterol level, lipid profile, electrolyte profile, prescription drug history, chest pain symptoms, history of sudden death in the family, rate of ventricular tachycardia, drug abuse, ventricular tachycardia morphology and PVC count or any combination thereof.

10. The method of claim 7, wherein the step of calculating the second set of data values produces data values selected from the group of: tachycardia detection rate, fibrillation detection rate, stability algorithms, fast ventricular tachycardia rate, bradycardia rate, stability algorithm settings, onset algorithms, individual therapies for each zone, and duration of therapies for each zone or any combination thereof.

11. The method of claim 7 further comprising the step of displaying the second set of data values on the programming device for operation confirmation.

* * * * *